United States Patent
Zhu et al.

(10) Patent No.: US 9,249,390 B2
(45) Date of Patent: Feb. 2, 2016

(54) METHOD FOR PRODUCING POLARIZED RETINAL PROGENITOR CELLS FROM PLURIPOTENT STEM CELLS AND THEIR DIFFERENTIATION INTO RETINAL PIGMENT EPITHELIUM CELLS

(75) Inventors: Yu Zhu, Dresden (DE); Elly Tanaka, Dresden (DE)

(73) Assignee: Technische Universitat Dresden, Dresden (DE)

( * ) Notice: Subject to any disclaimer, the term of this patent is extended or adjusted under 35 U.S.C. 154(b) by 1262 days.

(21) Appl. No.: 13/096,598

(22) Filed: Apr. 28, 2011

(65) Prior Publication Data

US 2011/0269173 A1 Nov. 3, 2011

(30) Foreign Application Priority Data

Apr. 28, 2010 (EP) .................................... 10161354

(51) Int. Cl.

| C12N 5/071 | (2010.01) |
|---|---|
| C12N 15/02 | (2006.01) |
| C12N 5/079 | (2010.01) |
| C12N 5/0797 | (2010.01) |
| C12N 5/0775 | (2010.01) |
| C12N 5/074 | (2010.01) |
| C12N 5/0735 | (2010.01) |
| C12N 5/0793 | (2010.01) |

(52) U.S. Cl.
CPC .............. *C12N 5/0621* (2013.01); *C12N 5/062* (2013.01); *C12N 5/0606* (2013.01); *C12N 5/0619* (2013.01); *C12N 5/0623* (2013.01); *C12N 5/0662* (2013.01); *C12N 5/0696* (2013.01); *C12N 2501/105* (2013.01); *C12N 2501/11* (2013.01); *C12N 2501/115* (2013.01); *C12N 2501/13* (2013.01); *C12N 2501/135* (2013.01); *C12N 2501/15* (2013.01); *C12N 2501/16* (2013.01); *C12N 2506/02* (2013.01); *C12N 2533/52* (2013.01)

(58) Field of Classification Search
CPC ............ C12N 2506/02; C12N 5/0606; C12N 2501/115; C12N 5/0696; C12N 2506/45; C12N 5/0623; C12N 2500/99; C12N 2501/16; C12N 2501/385; C12N 2533/90; C12N 5/0619; C12N 5/0621; C12N 2501/999; C12N 2533/52; C12N 5/0662; C12N 5/0618; C12N 5/0062; C12N 5/0603; C12N 5/0607; C12N 5/0672; C12N 2502/99; C12N 2506/11; C12N 2509/00; C12N 2799/027; C12N 5/0075; C12N 5/0676; C12N 5/0678; C12N 2500/02; C12N 2500/84; C12N 2500/90; C12N 2501/105; C12N 2502/02; C12N 2502/085; C12N 2502/086; C12N 2502/088; C12N 5/0018; C12N 5/0622; C12N 5/0677; C12N 5/068; C12N 5/0692
See application file for complete search history.

(56) References Cited

U.S. PATENT DOCUMENTS

2007/0196919 A1  8/2007 Reh et al.

FOREIGN PATENT DOCUMENTS

| EP | 2 128 244 A1 | 12/2009 |
| WO | WO 2011/055855 A1 | 5/2011 |

OTHER PUBLICATIONS

Lambda et al. Efficient generation of retinal progenitor cells from human embryonic stem cellsPNAS, 2006. vol. 103, pp. 12769-12774.*
Lambda et al. Generation, Purification and Transplantation of Photoreceptors Derived from Human Induced Pluripotent Stem Cells. PloS ONE, 2010, vol. 55(1), pp. 1-9, doi:10.1371/journal.pone.000876.*
Liu et al.A novel chemical-defined medium with bFGF and N2B27 supplements supports undifferentiated growth in human embryonic stem cells Biochem. Biophys. Res. Comm., 2006, vol. 346, pp. 131-139.*
Gamm et al. A Novel Serum-Free Method for Culturing Human Prenatal Retinal Pigment Epithelial Cells. Invest. Ophthalmol. Vis. Sci. 2008, vol. 49. pp. 788-799.*
Sun et al. Retinal stem/progenitor properties of iris pigment epithelial cells Develop. Biol., 2006, vol. 289, pp. 243-252.*
Jaffe et al. Activin Expression by Cultured Human Retinal Pigment Epithelial CellsInvest Ophthalmol Vis Sci. 1994;35:2924-2931.*
Stern et al. Stem Cell Retinal Replacement Therapy. 2010 Workd Stem Cell Summit. World Stem Cell Report, 2009 pp. 57-61.*

(Continued)

*Primary Examiner* — Deborah Crouch
(74) *Attorney, Agent, or Firm* — Sterne, Kessler, Goldstein & Fox PLLC

(57) ABSTRACT

The present invention relates to a method and components for producing polarized retinal progenitor cells (RPC) from pluripotent stem cells in high yield and purity. The polarized retinal progenitor cells are preferably further differentiated with high efficiency and speed into retinal pigment epithelium cells (RPE cells). The cells obtained are particularly suitable for use in cell transplantation or in the generation of transplant tissue and are particularly applicable to screening systems for substances that modulate the function of polarized retinal progenitor cells and/or RPE cells.

Figure 1:
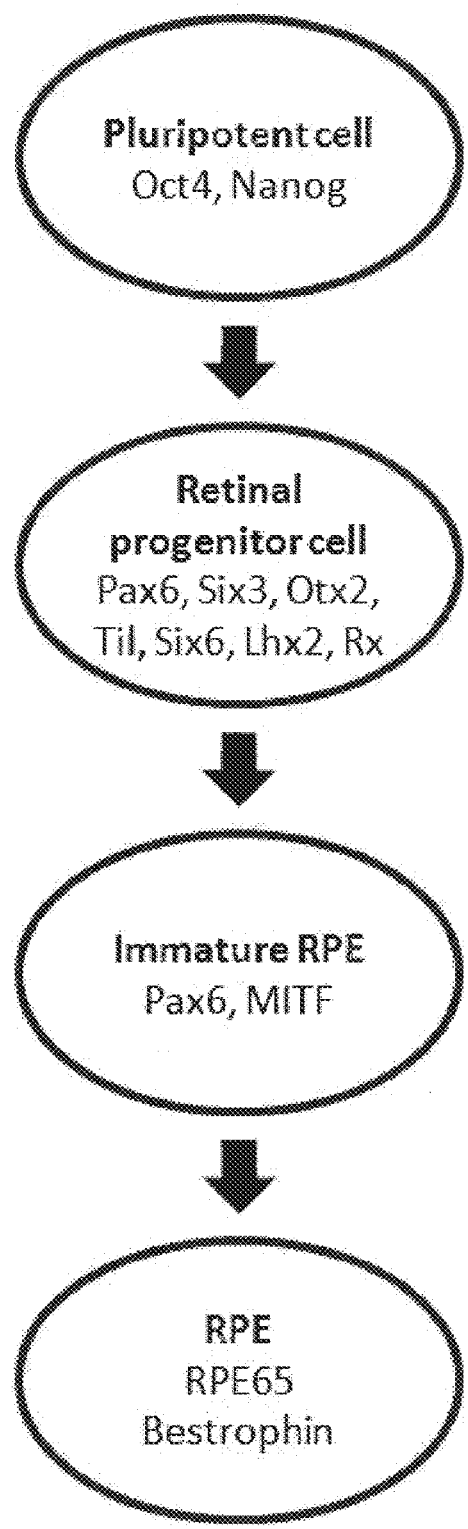

In the method according to the invention pluripotent stem cells are differentiated into polarized retinal progenitor cells by first culturing pluripotent stem cell colonies in three-dimensional cell culture embedded in a proteinaceous gel comprising at least two proteins selected from the group consisting of Laminin, Collagen IV Entactin and Perlecan and comprising at least two growth factors selected from agonists of the EGF, FGF2, NGF, PDGF, IGF-1 and TGF-beta pathways until polarized neural cysts develop and subsequently dissociating the polarized neural cysts into dispersed polarized retinal progenitor cells.

16 Claims, 10 Drawing Sheets

(56) References Cited

OTHER PUBLICATIONS

Gong, J., et al., "Effects of extracellular matrix and neighboring cells on induction of human embryonic stem cells into retinal or retinal pigment epithelial progenitors," *Experimental Eye Research* 86:957-965, Elsevier Ltd., USA (2008).

Ho, S.T.B., et al., "The influence of fibrin based hydrogels on the chondrogenic differentiation of human bone marrow stromal cells," *Biomaterials* 31:38-47, Elsevier Ltds., USA (2010).

Khetan, S. and Burdick, J., "Cellular Encapsulation in 3D Hydrogels for Tissue Engineering," *Journal of Visualized Experiments* 32: pii 1590, Journal of Visualized Experiments, USA (2009).

Lawrence, B.J., et al., "Multilayer composite scaffolds with mechanical properties similar to small intestinal submucosa," *Journal of Biomedical Materials Research Part A* 88A:634-643, Wiley Periodicals, Inc., USA (2008).

* cited by examiner

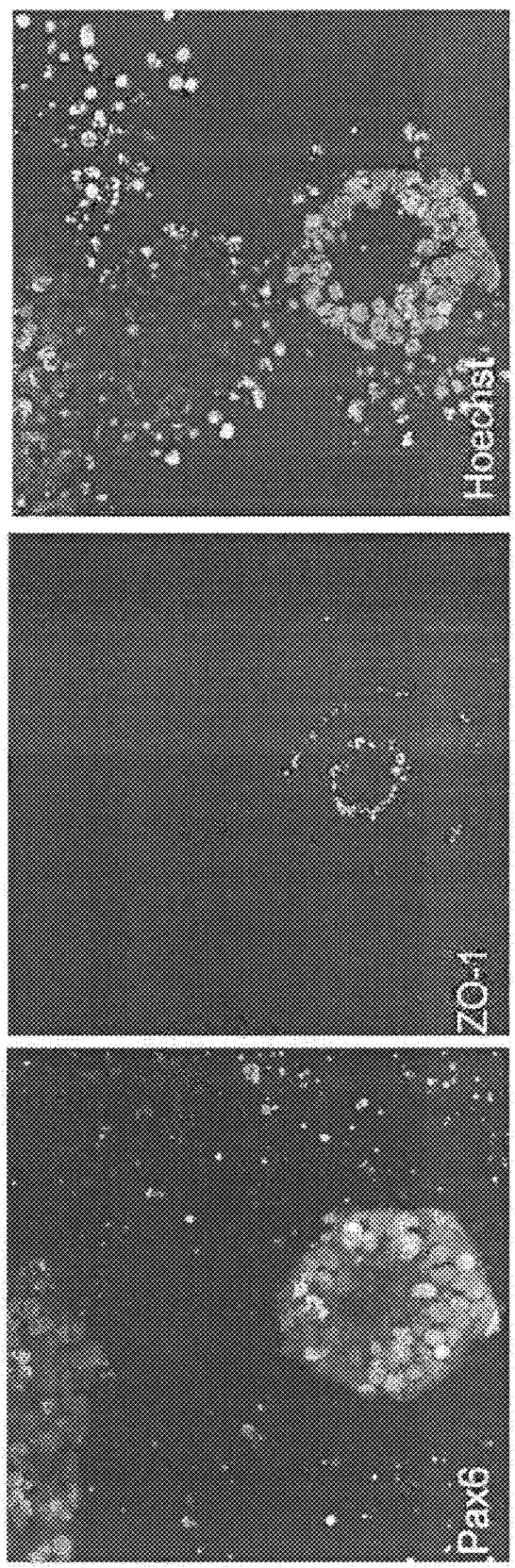

METHOD FOR PRODUCING POLARIZED RETINAL PROGENITOR CELLS FROM PLURIPOTENT STEM CELLS AND THEIR DIFFERENTIATION INTO RETINAL PIGMENT EPITHELIUM CELLS

The present invention relates to a method and components for producing polarized retinal progenitor cells (RPC) from pluripotent stem cells in high yield and purity. The polarized retinal progenitor cells are preferably further differentiated with high efficiency and speed into retinal pigment epithelium cells (RPE cells). The cells obtained are particularly suitable for use in cell transplantation or in the generation of transplant tissue and are particularly applicable to screening systems for substances that modulate the function of polarized retinal progenitor cells and/or RPE cells.

The retina is a layer of specialized light sensitive neural tissue located at the inner surface of the eye of vertebrates. Light reaching the retina after passing the cornea, the lens and the vitreous humor is transformed into a cascade of chemical and electrical events that ultimately trigger nerve impulses. The cells that are responsible for taking up light and converting it into the beginning of a chain of biological processes, a process that is called phototransduction, are specialized neurons which are called photoreceptor cells.

The retinal pigment epithelium (RPE) is a polarized monolayer of densely packed hexagonal cells in the mammalian eye that separates the neural retina from the choroid. The cells in the RPE contain pigment granules and perform a crucial role in retinal physiology by forming a blood-retinal barrier and closely interacting with photoreceptors in the maintenance of visual function by absorbing the light energy focused by the lens on the retina, by transporting ions, water, and metabolic end products from the subretinal space to the blood and by taking up nutrients such as glucose, retinol, and fatty acids from the blood and delivering these nutrients to photoreceptors. RPE cells are also part of the visual cycle of retinal: Since photoreceptors are unable to reisomerize all-trans-retinal, which is formed after photon absorption, back into 11-cis-retinal, retinal is transported to the RPE where it is reisomerized to 11-cis-retinal and transported back to the photoreceptors.

Since many ophthalmic diseases, such as (age-related) macular degeneration, macular dystrophies such as Stargardt's and Stargardt's—like disease, Best disease (vitelliform macular dystrophy), adult vitelliform dystrophy or subtypes of retinitis pigmentosa, are associated either with a degeneration or deterioration of the retina itself or of the RPE, there is a high interest in finding ways to produce RPE cells from human pluripotent stem cells as a source for cell transplantation for the treatment of retinal degenerative diseases. It has been demonstrated in animal models that photoreceptor rescue and preservation of visual function could be achieved by subretinal transplantation of RPE cells (Coffey, P J et al. Nat. Neurosci. 2002:5, 53-56; Lin, N et al. Curr. Eye Res. 1996:15, 1069-1077; Little C W et al. Invest. Ophthalmol. Vis. Sci. 1996:37, 204-211; Sauve, Y et al. Neuroscience 2002:114, 389-401.)

During early embryonic development the retinal primordia form in the rostral-most diencephalic region as marked by the expression of the transcription factor OTX2. The anterior neuroepithelium evaginates to give rise to the optic vesicle, followed by invagination that elaborates a bilayered optic cup. The eye field is molecularly definable due to the expression of a combination of transcription factors such as Pax6, Rx and Six3 (FIG. 1). The outer layer of the optic cup differentiates into the RPE, as discernable at early stages by the expression of MiTF (microphthalmia-associated transcription factor), whereas the inner layer differentiates into the neural retina as discernable by continued expression of Rx and of Chx10. The development of the layered vertebrate neural retina is a conserved process of cell genesis with the following order of cell birth: ganglion cells, horizontal cells, cone photoreceptors, amacrine cells, bipolar cells, rod photoreceptors and Müller glia.

Due to the defined sequence of steps and available diagnostic markers for RPE development, retinal progenitor cells and their differentiated descendents have been produced in cell culture from mouse, monkey and human embryonic and induced pluripotent stem cells by exposing them to different culture conditions. Such methods provide a potential means to produce transplantable cells for retinal degenerative diseases as described above and for in vitro screening pharmaceutical molecules on patient-specific induced pluripotent stem cells as a curative strategy. Pluripotent stem cells are a particularly good cell type for retinal progenitor cell production due to their unlimited expandability with stable karyotype, and the ability to make pluripotent stem cells from human patient samples. However, the current methods for differentiating human pluripotent stem cells into retinal progenitors, and further into RPE including differentiated cell types such as photoreceptors are inefficient and lengthy, limiting their effective use for transplantation and drug screening.

Embryonic stem cells (ES cells) are pluripotent cells that can be propagated in cell culture and stably maintain the ability to differentiate into all three embryonic germ layers. They also stably retain a normal karyotype, thus providing a powerful source for forming different cell types in vitro.

In classic protocols ES cells were isolated from the inner cell mass of the mouse blastocyst. (Martin 1981, Proc. Natl. Acad. Sci. USA 78: 7634-7638; Evans & Kaufman 1981, Nature 292: 154-156) and can today be obtained from a large number of species including humans. In newer protocols, however, ES cells can be obtained without destruction of a blastocyst. In one protocol, for instance, this is achieved based on the outgrowth of single blastomeres derived from blastocysts using a technique similar to preimplantation genetic diagnosis (PGD), as described by Chung Y et al. (Cell Stem Cell 2008 (2): 113-117+supplemental material). Other studies have shown that ES-Cells can be obtained by parthenogenesis, e.g. from a one-pronuclear oocyte (Lin et al. 2007. Cell Res 2007; 17:999-1007), or parthenogenetic activation of human oocytes (Mai et al. 2007. Cell Res 17:1008-1019).

Recently, it has been possible to produce pluripotent cells from adult human and mouse cells by providing a defined number of transcription factors to the cells (Takahashi K. et al. Cell 2007:131, 861-872; Yu J et al. Science 2007:318, 1917-1920). These induced pluripotent stem cells (iPS cells) are remarkably similar to embryonic stem cells, express similar molecular markers, and display pluripotency. In addition to transcription factor induced pluripotent cells, so called germline Embryonic Stem cells (gESC) have been derived from mouse and possibly human germline stem cells without the use of embryos. Both iPS cells and gESC are functionally equivalent or very similar to ES cells, and can be used to form various differentiated cell types in vitro.

Mouse, monkey, and human ES cells have been implemented for retinal differentiation as well as human iPS cells. For differentiation of cells into RPE, two different classes of protocols have been developed. One relies on random differentiation of human embryonic stem cells or induced pluripotent stem cells in serum- or serum-substitute containing media (Vugler A et al. Exp Neurol. 2008 December; 214(2): 347-61; Klimanskaya I et al. Cloning Stem Cells. 2004; 6(3): 217-45; Buchholz D E et al. Stem Cells. 2009 October; 27(10) 2427-34). The rate of such cells that spontaneously differentiate into RPE cells is extremely low, less than 1%. The reason why some cells turn into RPE cells while others do not is unclear. The RPE cell clones are then picked manually and expanded, a process that takes at least six weeks, if not longer. The other class of protocols starts by forming floating aggregrates. Idelson et al. (Cell Stem Cell 2009:5, 396-408) disclose a method of directing differentiation of human embryonic stem cells into functional RPE cells, which employ nicotinamide and Activin A to induce and augment differentiation into RPE cells. For differentiation, hESC colonies were cultured as floating clusters in knockout serum containing medium supplemented with 10 mM Nicotinamide in 6-well culture dishes which were pretreated with 0.1% low-melting-temperature agarose. Activin A (20-180 ng/ml) was supplemented during the third and fourth weeks to increase the appearance of pigmented clusters. For expansion as a monolayer, after 8 weeks in suspension, pigmented areas were mechanically picked up, triturated and plated on poly-D-lysine and laminin-coated dish and cultured in knockout medium+NIC. This protocol takes a long time to achieve typical monolayer of hexagonal RPE cells, while yield and efficiency are low. After 4 weeks of suspension culture with NIC and Activin A, the yield of RPE-like pigmented cells is approximately 10%. The expansion of pigmented area as a monolayer requires about 14 weeks in total.

Meyer et al describe a protocol starting with floating aggregates followed by plating for RPE differentiation (Meyer J S et al. PNAS 2009:106, 16698-703). The undifferentiated human ES or iPS cells were grown as aggregates in suspension in knockout serum-containing medium to initiate differentiation. The aggregates were then switched to serum free neural induction medium supplemented with N2. After the initial 6 days of suspension culture, aggregates were allowed to attach laminin coated culture dish. During the adhesive culture, the medium was changed from N2 supplement-containing neural induction medium to serum free medium supplemented with B27 on day 16 of differentiation. In this protocol 25% of cells attain RPE identity (as defined by MiTF+staining) by day 40. The purity of RPE cells derived from human ES or iPS cells is low based on this protocol.

US 2007/0196919 A1 describes methods for the in vitro differentiation of human retinal progenitor cells from embryonic stem cells by the steps: a. culturing ES cells to embryoid bodies in the presence of a cocktail of factors that direct differentiation to an anterior neural fate, b. culturing said embryoid bodies in retinal differentiation medium comprising an antagonist of bone morphogenetic protein (BMP) signaling pathways; an antagonist of wnt signaling pathways; an IGF1R agonist; and a molecule that provides FGF2 activity. Preferably said embryoid bodies are plated to adhere to a semi-solid substrate prior to culturing in retinal differentiation medium. The cocktail of factors that direct differentiation to an anterior neural fate comprises an antagonist of bone morphogenetic protein (BMP) signaling pathways; an antagonist of wnt signaling pathways; and an IGF1R agonist, in the absence of basic fibroblast growth factor (FGF2) activity.

However, the patterning of in vitro differentiated retinal cells is still far away from the in vivo layered structure of the neural retina (Osakada F et al. Nature Protocols 2009:4, 811-824; Lamba D A et al. PNAS 2006:34, 12769-74; Meyer J S et al. PNAS 2009:106, 16698-703; Lamba D A et al. Plos One 2010:5, e8763).

EP 2 128 244 A1 describes a method of producing primate retinal progenitor cells by culturing primate embryonic stem cells as suspended aggregates in a serum-free medium, and obtaining retinal progenitor cells from the culture. Preferably the serum-free medium contains a Nodal signal inhibitor and a Wnt signal inhibitor. It further describes a method of producing photoreceptor precursor cells by culturing isolated retinal progenitor cells differentiated from embryonic stem cells, under adhesive conditions, in the presence of a gamma secretase inhibitor, and obtaining a photoreceptor precursor from the culture. The efficiency of generating retinal progenitor cells from ES cells based on this method is low. Less than 30% of the differentiated cells are positive for the retinal progenitor cell markers such as Rx, Pax6 and MiTF. Besides, this method takes long time to achieve RPE cells and photoreceptor precursor cells (i.e. $Crx^+$ cells). Human ES cell-derived pigment cells obtained by this method formed tight junctions and had the structural characteristics of RPE by day 120. $Crx^+$ photoreceptor precursor cells derived from human ES cells were observed on day 90.

Osakada F et al. (Nat. Biotechnol. 2008:26(2), 215-224) disclose that the differentiation of RPE cells and photoreceptor cells can be induced by culturing mouse, monkey and human ES cells by stepwise treatments under defined conditions. With human ES cells, feeder- and serum-free suspension culture combined with Dkk1 and LeftyA induced differentiation of Rx+ or MiTF+retinal progenitors, which produced RPE cells under adhesive conditions.

Lamba et al. (PNAS 2006:34, 12769-74) describe a method for retinal induction by treating embryoid bodies with a combination of noggin, Dickkopf-1 and IGF-1. The differentiating hESCs were cultured as embryoid bodies for 3 days in the three factors containing medium and then transferred to six-well plates coated with poly-D-lysine-Matrigel where they were allowed to attach. The cells were then maintained in the presence of DMEM:F12, B27 supplement, N2-supplement, noggin, Dkk-1, IGF-1 and bFGF for an additional 3 weeks. This protocol mainly focuses on the neural retina cell differentiation of hESCs.

Hirano M et al. (Dev. Dyn. 2003:228(4), 664-671) describe a stromal cell PA6-dependent culture system in which a eye-like structure consisting of cells corresponding to lens, neural retina, and pigmented retina was efficiently induced from mouse embryonic stem cells using serum containing medium supplemented with bFGF, cholera toxin and dexamethasone. However, unlike the normal eye composed of a separate lens and an organized layered structure of individual retinal cell types, most of the retinal cell types were mixed within the multilayered cell masses induced from mouse ES cells using this method. Furthermore, Aoki H et al. have proved that this method couldn't be applied for human ES cells. The efficiency of generating retinal cells by co-cultures of human ES cells and PA6 stromal cells using the same procedures was very low and disadvantageous for further analysis. (Aoki H et al. Dev Dyn. 2009 September; 238(9):2266-79.)

The current published protocols for differentiation of pluripotent stem cells into RPC or RPE are summarized in Table 1:

TABLE 1

| Paper/Related patent document | Stem cell source | RPE or RPC | Essential method | Time | Efficiency |
|---|---|---|---|---|---|
| Klimanskaya I et. al. (Vugler A) | Human, ES | RPE | Spontaneous differentiation, 60 days | 60 days | >1% |
| Buchholz DE et al. | Human, iPS | RPE | Spontaneous differentiation, 60 days | 60 days | >1% |
| Idelson et al. | Human ES | RPE | Floating aggregate + activin and NIC, | 8 weeks | 4% |
| Hirano et al. | Mouse | RPE | Coculture with PA6 cells | 11 Days | mixture with other eye tissues |
| Meyer JS et al. | Human | RPC, RPE | Floating aggregates | 16 Days 40 Days | >95% Rx+ 25% MiTF |
| Osakada et al./ EP 2 128 244 A1 | Primate, ES | RPC, RPE | Floating aggregate DKK1, Lefty, SB431542, CKI-7 | 50 Days 120 Days | 31% MiTF+ 34% ZO1+ |
| Ikeda et al. | Mouse | RPC, | Floating aggregate + Dkk1 and Lefty | 7 days | 16% Rx+ |
| Lamba et al./ US2007/0196919 | Human, ES | RPC | Floating aggregate + IGF, Dkk1, noggin | 21 days | 80% Chx10 |

In summary, the known procedures to produce retinal progenitor cells or RPE cells have many disadvantages. They take many weeks to obtain differentiated cells and their efficiency is very low.

Thus there remains a need for improved methods of differentiating pluripotent stem cells into RPE cells.

According to one aspect of the present invention there is provided a method for differentiating pluripotent stem cells into polarized retinal progenitor cells, comprising the steps:
a) culturing pluripotent stem cell colonies in three-dimensional cell culture embedded in a proteinaceous gel comprising at least two, preferably at least three proteins selected from the group consisting of Laminin, Collagen IV, Entactin and Perlecan and comprising at least two, preferably at least three, most preferably at least four growth factors selected from agonists of the EGF, FGF2, NGF, PDGF, IGF-1 and TGF-beta pathways, preferably selected from EGF, FGF2, NGF, PDGF, IGF-1 and TGF-beta, until polarized neural cysts develop and
b) dissociating the polarized neural cysts into dispersed polarized retinal progenitor cells.

The inventors surprisingly found that by culturing pluripotent stem cell colonies embedded in a proteinaceous gel polarized cysts of retinal progenitor cells can be obtained. Advantageously a high percentage of these cells can be further differentiated to Retinal Pigment Epithelium (RPE) cells by culturing them further in RPE medium.

Another advantage of the present invention in comparison to known methods is that since the single-cell retinal progenitor cells obtained by dissociation of the cysts have all approximately the same age, it is possible to prepare RPE cells that have a defined age.

The pluripotent stem cell colonies that are used for the method according to the invention can be obtained by culturing methods known in the state of the art. Human ES cells and iPS cells are growing as colonies under adhesive conditions. The cell colonies can be used directly for the method according to the invention. Optionally they can be partially dissociated into smaller clumps with enzymatic treatment (e.g. Dispase).

The cysts that are obtained by the method according to the invention are highly organized structures. They contain a lumen, i.e. a liquid filled cavity inside the cyst, and consist of polarized cells. The basal side of the cells in the cyst points towards the outside of the cyst, while the apical side points towards the lumen. They are not to be confused with embryoid bodies known from the state in the art, which are ordinarily used to initiate the in vitro differentiation of hESCs/iPSCs. Embryoid bodies represent a mixture of different cell types—including cells of different germlayer origin such as mesoderm, endoderm and ectoderm. However, they are not as organized, polarized and defined as the cysts obtained by the method according to the invention. During the formation of embryoid bodies, these contain a mixture of cells of different ages and at different developmental stages. The cysts are also not to be confused with floating aggregates in liquid culture such as are described by Idelson et al., Meyer J S et al. or Osakada et al. The polarized neural cysts are then dissociated into dispersed polarized retinal progenitor cells by known means. Dissociated or dispersed polarized retinal progenitor cells mean a preparation or suspension of cells that is comprised of single cells or clusters containing a maximum of 7, preferably 2 to 3 cells.

Consequently the present invention also provides a method for differentiating the polarized retinal progenitor cells into retinal pigment epithelium (RPE) cells by culturing the single cells that are obtained by dissociation of the polarized neural cysts in two-dimensional cell culture, preferably in coated wells, using a culture medium that is supplemented with Activin A.

In the present context, the term "cell culture" refers to any in vitro culture of cells. Included within this term are continuous cell lines (e.g. with an immortal phenotype), primary cell cultures, finite cell lines (e.g. non-transformed cells), and any other cell population maintained in vitro, including oocytes and embryos.

As used herein, "two-dimensional cell culture" is intended to indicate conventional two-dimensional (2D) culture wherein adherent cells are cultured in a monolayer on a two-dimensional surface.

As used herein, "three-dimensional cell culture" is intended to indicate a tissue culture model that mimics in vivo tissue architecture through culturing cells embedded in a proteinaceous gel which mimics an extracellular matrix.

As used herein, the term "proteinaceous gel" is intended to indicate a hydrogel structure comprised of a network of proteins, preferably fibrous proteins, which are dispersed in a aqueous solvent, preferably a suitable cell culture medium. In the proteinaceous gel, further proteinaceous and non-proteinaceous components can be present, such as growth factors or polysaccharides such as Glycosaminoglycans (e.g. heparan sulfate, heparin, hyaluronan, keratan sulfate, dermatan sulfate, chondroitin sulfate).

The starting materials for the method according to the invention are pluripotent stem cells. The pluripotent stem cells are preferably of vertebrate, in particular mammalian, preferably human, primate or rodent origin. Preferred pluripotent cells are selected from embryonic stem cells, induced pluripotent stem cells, stem cells derived from the amniotic fluid or stem cells derived from fetuses, in particular embryonic germ cells derived from fetuses, germline stem cells (in particular from the testes) and pluripotent somatic stem cells.

Potential sources of pluripotent cells include stem cells obtained from the amnion and/or the cord blood, gESCs, i.e. embryonic stem cell-like cells derived from the testes (Kanatsu-Shinohara M et al. Ann N Y Acad. Sci. 2007 December; 1120:59-71; Conrad S et al. Nature. 2008 Nov. 20; 456(7220):344-9; Guan K et al. Nature Protocols. 2009; 4(2): 143-54) and very small embryonic-like (VSEL) stem cells (Kucia M et al. Leukemia. 2006 May; 20(5):857-69).

As used herein, the term "pluripotent stem cell" or "pluripotent cell" is intended to indicate a cell that has preferably the potential to differentiate into any of the three germ layers: endoderm (interior stomach lining, gastrointestinal tract, the lungs), mesoderm (muscle, bone, blood, urogenital), or at least the ectoderm (epidermal tissues and nervous system). Thus, preferably pluripotent stem cells can give rise to any fetal or adult cell type. For carrying out the invention it is important that stem cells used have the ability to form cells of the ectoderm and in particular to form cells from the nervous system.

The term "pluripotent cells" can include totipotent cells, i.e. cells that can divide and produce all the differentiated cells in an organism, including extraembryonic tissues. For ethical reasons, however, totipotent cells that are derived from human sources, in particular human embryos, are preferably excluded.

Preferred pluripotent stem cells are characterized by the expression of the following molecular markers: Oct-4, Nanog, KLF4, ESRRB, TDGF1 (also known as CRIPTO), Sox2 and c-Myc (also known as MYC). One preferred example of pluripotent stem cells are embryonic stem cells (ES cells). The invention as defined by the claims does not involve the destruction of human embryos. Preferably, ES cells are derived from mammals, more preferably from mice, rats, rabbits, guinea pigs, goats, pigs, cows, monkeys and humans. Human and murine or rat derived ES cells are preferred. Preferably the invention does not involve the use of human embryos for industrial or commercial purposes.

Another preferred example of pluripotent stem cells are induced pluripotent stem cells. As used herein, the term "iPS cell" or "induced pluripotent stem cell" is intended to indicate stem cell-like pluripotent cells which are derived from reprogrammed somatic cells (see for instance Takahashi K. et al. Cell 2007:131, 861-872; Yu J et al. Science 2007:318, 1917-1920; Feng, B et al. Cell Stem Cell 2009:4, 301-312), preferably derived from a developed organism, such as adult fibroblasts.

In many respects induced pluripotent stem cells possess the same properties as natural pluripotent stem cells, such as the expression of certain stem cell genes and proteins, chromatin methylation patterns, doubling time, embryoid body formation, teratoma formation, viable chimera formation, and potency and differentiability.

The transformation of non-pluripotent cells into pluripotent cells is achieved either by inducing a "forced" expression of certain stem cell-associated genes in the respective cell or by exposing the cells with the corresponding stem cell-associated proteins, preferably by channeling the proteins into the cells. Transfection is typically achieved through viral vectors, such as retroviruses, adenoviruses or lentiviruses, or through episomal vectors. Preferably, the cells are transfected with stem cell-associated genes selected from one or several (preferably 3 to 4) master transcriptional regulators selected from the group consisting of Oct-3/4, Sox1, Sox2, Sox3, Sox15, Sox18, c-Myc, N-myc, L-myc, Nanog, LIN28, Klf1 Klf2, Klf4, and Klf5, more preferably selected from the group consisting of Oct-3/4, Nanog, c-myc and Sox2. Alternatively the cells are exposed to the corresponding proteins.

Preferably, oncogenes like c-myc are removed after the induction of pluripotency, thereby increasing the potential use of iPS cells in human diseases. Even more preferably, the iPS cells used in the method according to the invention are so called piPS (protein-induced pluripotent stem cells), that is, they are generated by a repeated treatment of the cells with stem cell-associated proteins, preferably channeled into the cells via poly-arginine anchors (Zhou H. et al. Cell Stem Cell, Volume 4, Issue 5, 2009:381-384) or by fusing them to other cell penetrating peptides (CPP). The generation of iPS cells can be assisted by the use of pharmacological inhibitors or activators of certain pathways.

As used herein, the term "retinal progenitor cells" is intended to indicate progenitor cells that have the ability to differentiate into either RPE cells, neural retina cells, cells of the ciliary margin, ciliary pigment epithelium cells or cells of the dorsal and ventral optic stalk.

As used herein, the term "polarized retinal progenitor cells" is intended to indicate progenitor cells that have the ability to differentiate into either RPE cells or other cells of the retinal lineage, cells of the ciliary margin, ciliary pigment epithelium cells or cells of the dorsal and ventral optic stalk and show an apical-to-basal polarity that is one of the key characterizations of epithelia cells. Polarized retinal progenitor cells are positive for the expression of at least two, preferably at least three, more preferably four, of the following marker genes Rx, Pax6, Six3, ET, Lhx2, tll, Optx2, Otx2, MiTF, Chx10, ZO1, Prominin-1 and C-Cadherin, and negative for the expression of at least two, preferably at least three, more preferably four, of the following marker genes En1, Krox20, Gbx2, Hoxb1, Hoxc5 and Hoxc8.

As used herein, the term "retinal pigment epithelium (RPE) cells" is intended to indicate the pigmented cell layer just outside the neural retina, and are firmly attached to the underlying choroid and overlying retinal visual cells. RPE cells are positive for the expression of at least two, preferably at least three, more preferably four, of the following marker genes Pax6, MiTF, RPE65, Bestrophin, CRALBP, PEDF and ZO1 and negative for the expression of at least two, preferably at least three, more preferably four, of the following marker genes βIII tublin, NeuN, Chx10, Brn3a, Recoverin, Rhodopsin, Calbindin and Calretinin.

Preferred induced pluripotent stem cells are obtained by reprogramming fibroblast, neural, ectodermal and/or hair follicle cells. Preferably iPS cells from established iPS cell lines are used. Preferred established iPS cell lines are selected from the following list (table taken from Hu B Y et al. Proc Natl Acad Sci USA. 2010 Mar. 2; 107(9):4335-40):

| iPS-Lines | Sources | Cat# | Nature | Age | Sex | factors | Methods | Teratoma | Ref. |
|---|---|---|---|---|---|---|---|---|---|
| iPS(IMR90)-1 | IMR-90 | ATCC-CCL-188 | Lung_broblast | 16 weeks | F | OCT4, SOX2, NANOG, LIN28 | Lentivirus | Y | 1 |
| iPS(IMR90)-4 | IMR-90 | ATC-CCCL-188 | Lung_broblast | 16 weeks | F | OCT4, SOX2, NANOG, LIN28 | Lentivirus | Y | 1 |

-continued

| iPS-Lines | Sources | Cat# | Nature | Age | Sex | factors | Methods | Teratoma | Ref. |
|---|---|---|---|---|---|---|---|---|---|
| iPS-M4-10 | CCD-1090Sk | ATCC-CRL-2106 | Skin_broblast | 46 years | F | OCT4, SOX2, NANOG, LIN28 | Lentivirus | Y | 2 |
| iPS-M4-8 | CCD-1090Sk | ATCC-CRL-2106 | Skin_broblast | 46 years | F | OCT4, SOX2, NANOG, LIN28 | Lentivirus | Y | 2 |
| iPS-M3-6 | CCD-1090Sk | ATCC-CRL-2106 | Skin_broblast | 46 years | F | OCT4, SOX2, NANOG | Lentivirus | Y | 2 |
| iPS-DF6-9_9 | CCD-1079Sk | ATCC-CRL-2097 | Skin_broblast | Newborn | M | OCT4, SOX2, NANOG, LIN28, c-Myc, KLF4 | Episomal vectors | Y | 3 |
| iPS-DF6-9_12 | CCD-1079Sk | ATCC-CRL-2097 | Skin_broblast | Newborn | M | OCT4, SOX2, NANOG, LIN28, c-Myc, KLF4 | Episomal vectors | Y | 3 |
| iPS-DF19-9_11 | CCD-1079Sk | ATCC-CRL-2097 | Skin_broblast | Newborn | M | OCT4, SOX2, NANOG, LIN28, c-Myc, KLF4 | Episomal vectors | Y | 3 |
| iPS-DF19-9_19 | CCD-1079Sk | ATCC-CRL-2097 | Skin_broblast | Newborn | M | OCT4, SOX2, NANOG, LIN28, c-Myc, KLF4 | Episomal vectors | Y | 3 |
| iPS-DF4-3_7 | CCD-1079Sk | ATCC-CRL-2097 | Skin_broblast | Newborn | M | OCT4, SOX2, NANOG, LIN28, c-Myc, KLF4 | Episomal vectors | Y | 3 |
| iPS-108 | Coriell | GM03814 | Fibroblast | Adult | F | OCT4, SOX2, c-Myc, KLF4 | Retrovirus | NA | |
| iPS-109 | Coriell | GM03814 | Fibroblast | Adult | F | OCT4, SOX2, c-Myc, KLF4 | Retrovirus | NA | |

References (1-3):
1. Yu J, et al. (2007) Induced pluripotent stem cell lines derived from human somatic cells. Science 318: 1917-1920.
2. Choi KD, et al. (2009) Hematopoietic and endothelial differentiation of human induced pluripotent stem cells. Stem Cells 27: 559-567.
3. Yu J, et al. (2009) Human induced pluripotent stem cells free of vector and transgene sequences. Science 324: 797-801.

Preferably, ES cells from established ES cell lines are used. Preferred established ES cell lines are selected from the following list:

| Designation | Provider | Organism |
|---|---|---|
| ES-C57BL/6 | ATCC SCRC-1002 | *Mus musculus* (mouse) |
| J1 | ATCC SCRC-1010 | *Mus musculus* (mouse) |
| R1 | ATCC SCRC-1011 | *Mus musculus* (mouse) |
| RW.4 | ATCC SCRC-1018 | *Mus musculus* (mouse) |
| B6/BLU | ATCC SCRC-1019 | *Mus musculus* (mouse) |
| SCC#10 | ATCC SCRC-1020 | *Mus musculus* (mouse) |
| EDJ#22 | ATCC SCRC-1021 | *Mus musculus* (mouse) |
| AB2.2 | ATCC SCRC-1023 | *Mus musculus* (mouse) |
| Ainv15 | ATCC SCRC-1029 | *Mus musculus* (mouse) |
| 7AC5/EYFP | ATCC SCRC-1033 | *Mus musculus* (mouse) |
| R1/E | ATCC SCRC-1036 | *Mus musculus* (mouse) |
| G-Olig2 | ATCC SCRC-1037 | *Mus musculus* (mouse) |
| CE-1 | ATCC SCRC-1038 | *Mus musculus* (mouse) |
| CE3 | ATCC SCRC-1039 | *Mus musculus* (mouse) |
| hESC BG01V | ATCC SCRC-2002 | *Homo sapiens* (human) |
| SCED 461 | Cellartis, Göteborg, SE | *Homo sapiens* (human) |
| SA01 (SA001) | WiCell, Cellartis, Göteborg, SE | *Homo sapiens* (human) |
| SA02 (SA002) | WiCell, Cellartis, Göteborg, SE | *Homo sapiens* (human) |
| ES01 (HES-1) | WiCell, ESI | *Homo sapiens* (human) |
| ES02 (HES-2) | WiCell, ESI | *Homo sapiens* (human) |
| ES03 (HES-3) | WiCell, ESI | *Homo sapiens* (human) |
| ES04 (HES-4) | WiCell, ESI | *Homo sapiens* (human) |
| ES05 (HES-5) | WiCell, ESI | *Homo sapiens* (human) |
| ES06 (HES-6) | WiCell, ESI | *Homo sapiens* (human) |
| BG01 (BGN-01) | WiCell, ESI | *Homo sapiens* (human) |
| BG02 (BGN-02) | WiCell, ESI | *Homo sapiens* (human) |
| BG03 (BGN-03) | WiCell, ESI | *Homo sapiens* (human) |
| TE03 (I3) | WiCell, ESI | *Homo sapiens* (human) |
| TE04 (I4) | WiCell, ESI | *Homo sapiens* (human) |
| TE06 (I6) | WiCell, ESI | *Homo sapiens* (human) |
| UC01 (HSF1) | WiCell, ESI | *Homo sapiens* (human) |
| UC06 (HSF6) | WiCell, ESI | *Homo sapiens* (human) |
| WA01 (H1) | WiCell, ESI | *Homo sapiens* (human) |
| WA07 (H7) | WiCell, ESI | *Homo sapiens* (human) |
| WA09 (H9) | WiCell, ESI | *Homo sapiens* (human) |
| WA13 (H13) | WiCell, ESI | *Homo sapiens* (human) |
| WA14 (H14) | WiCell, ESI | *Homo sapiens* (human) |
| iPS-DF19-9 | WiCell, ESI | *Homo sapiens* (human) |
| iPS-DF4-3 | WiCell, ESI | *Homo sapiens* (human) |
| iPS-DF6-9 | WiCell, ESI | *Homo sapiens* (human) |
| iPS (Foreskin) | WiCell, ESI | *Homo sapiens* (human) |
| iPS (IMR90) | WiCell, ESI | *Homo sapiens* (human) |
| MEL-1 | Millipore | *Homo sapiens* (human) |
| MEL-2 | Millipore | *Homo sapiens* (human) |

ATCC = American Type Culture Collection, VA, USA
ESI = ES cell International PtE Ltd, Singapore
WiCell = WiCell Research Institute, Madison, WI, USA Human Embryonic Stem Cell Lines
Millipore = Millipore Corporation, 290 Concord Road, Billerica, MA 01821, USA Further established human ES cell lines (e.g. as described in Cowan, C. A. et. al, (New England Journal of Medicine. 2004. 350; 13ff.) are obtainable from the Human Embryonic Stem (HUES) Cell Collection, HUES Facility/Melton Laboratory/HHMI Harvard University Cambridge, Mass. 02138, USA and the WiCell Research Institute, Madison, Wis., USA.

An overview of the presently available human ES cell lines is given in Loeser P et al. Stem Cells 2010; 28:240-246) and supplementary data.

A particularly preferred human ES cell line is H9 (WA09).

For neural differentiation, colonies of pluripotent cells are partially dissociated into clumps with suitable enzymes such as Collagenase or Dispase, if necessary. The diameter of the cell clumps is preferably in the range of 20-200 μm, particularly preferred are cell clumps with a diameter in the range of 50-100 μm. The cell clumps are preferably washed once with cell culture medium.

Preferably between $2\times10^5$ to $10\times10^5$, more preferably $3\times10^5$ to $5\times10^5$, cells are embedded in a volume of 100 to 1000 μl, preferably 200 to 500 μl, more preferably 250 to 350 μl of a proteinaceous gel.

The proteinaceous gel is comprised of at least two, preferably at least three proteins selected from the group consisting of Laminin, Collagen IV, Entactin and Perlecan. Preferably the proteinaceous gel is comprised of extracellular matrix proteins, more preferably basement membrane proteins. Even more preferable matrigel, a commercially available gelatinous protein mixture secreted by Engelbreth-Holm-Swarm (EHS) mouse sarcoma cells, is used as proteinaceous gel. Matrigel is a gelatinous protein mixture that resembles the complex extracellular environment found in many tissues and is used by cell biologists as a substrate for cell culture, especially as an attachment substrate in embryonic stem cell culture, to maintain the pluripotent, undifferentiated state of embryonic stem cells in the absence of feeder cells.

The proteinaceous gel further comprises at least two, preferably three, most preferably four, growth factors selected from agonists of the EGF, FGF2, NGF, PDGF, IGF-1 and TGF-beta pathways, preferably selected from EGF, FGF2, NGF, PDGF, IGF-1 and TGF-beta. One particular preferred component is IGF-1. The proteinaceous gel in which the pluripotent cell clumps are embedded is then plated as gel layer of about 0.5 to 5 mm, preferably 1 to 2 mm thickness onto dishes.

After allowing the proteinaceous gel to gel, a cell culture medium suitable for neural differentiation further referred to as neural differentiation medium or NDM is added to the dish. The neural differentiation medium is preferably an essentially serum free medium containing at least two, preferably at least three, components selected from the group consisting of Insulin, Transferrin, Progesterone, Putrescine and a Selenite salt, more preferably at least Transferrin and Insulin. The proteins are preferably isolated native proteins or produced recombinant. Preferred examples for NDM are cell culture media containing selected from the group consisting of N2, B27, N2B27 and/or G5 supplement.

As used herein, the term "essentially serum-free" is intended to indicate a medium that comprises less than or equal to 2% serum, preferably less than or equal to 1% serum, more preferably less than or equal to 0.5% serum, and more preferably still, no serum.

As used herein, the term "serum containing medium" is intended to indicate a medium that comprises at least 5% serum, preferably about 5% to 15% serum, but possibly higher, e.g. 20% or more.

The serum-free medium or essentially serum-free medium advantageously does not require addition of a Nodal signal inhibitor (like Dkk), a Wnt signal inhibitor (like Lefty) and a BMP signal inhibitor (like Noggin) or other special factors like retinoic acid, taurine and Nicotinamide.

The pluripotent cells are cultured for 4 to 7, preferably 5 to 6 days, until they form polarized neural cysts which consist of polarized neural progenitor cells.

Compared to protocols known in the state of the art (e.g. as disclosed in Lamba et al), the method according to the invention uses three dimensional cell culture in a proteinaceous gel matrix to induce cell polarity and thus advantageously results in a high percentage of polarized retinal progenitors after only 4 to 7 days of differentiation.

At this stage, the vast majority of the cells co-express Rx and Pax6. The expression of Prominin-1 and ZO-1 is restricted to the apical side of the cysts. The cell polarity is confirmed by interkinetic nuclear migration, i.e. the apical—basal movement of nuclei in phase with the cell cycle, which is one important polarized feature of different cell types that arise during neurodevelopment, such as neuroepithelial cells, radial glia cells or basal progenitors.

For differentiation into retinal pigment epithelium (RPE) cells, the polarized neural cysts are taken out of the proteinaceous gel by incubation with cell recovery solution on ice. Preferably, they are washed once or several times in the culture medium.

The polarized neural cysts are then dissociated into single cells. In the context of the present invention the term "dispersed cells" is intended to indicate not only single cells, but also includes clusters of up to seven, more preferably up to five, even more preferably up to three cells. Methods to dissociate neural cysts are known in the state of the art. For instance, incubation with enzymes like TrypLE, Trypsin (EDTA), Accutase, Dispase or Collagenase optionally in combination with flipping of the container, pipetting the cell suspension up and down, passing the cell suspension through a cell strainer are methods that may be used to obtain single cells.

Compared to methods known in the state in the art (see table 1), the method according to the invention advantageously succeeds to differentiate a high percentage of cells into retinal progenitor cells. After only 5 days of culturing in three dimensional cell culture more than 90% of cells co-express Rx and Pax6.

To obtain RPE cells, the retinal progenitor cells obtained by the steps described above are plated onto plates, preferably transwell filters, that are preferably precoated with a proteinaceous gel, such as gelatin, laminin, poly-D-lysine, Bruch's membrane explant or fibronectin.

More preferably said proteinaceous gel used for precoating the wells is growth factor reduced, i.e. the concentration of growth factors within the gel is reduced compared to the protein mix in its original state, or lacks growth factors completely. The plates are even more preferably precoated with growth factor reduced matrigel.

In a preferred embodiment of the invention, the dissociated retinal progenitor cells are plated onto a permeable microporous membrane or support, preferably of polyester and/or polycarbonate, that can be placed in a dish or a well containing cell culture medium, allowing the cells to attach to a support while being surrounded by medium, allowing polarized cell growth. Preferably the permeable microporous membrane is coated with a proteinaceous gel, preferably growth factor reduced matrigel.

Preferably the retinal progenitor cells are plated with a density of $1 \times 10^5$ to $6 \times 10^5$ cells/0.3 cm$^2$ (cell growth area), more preferably $2 \times 10^5$ to $4 \times 10^5$ cells/0.3 cm$^2$ (cell growth area).

Preferably the retinal progenitor cells are grown in NDM for about one more day to allow the cells to adapt to the new environment.

Subsequently, the attached cells are cultivated in a medium suitable for maintaining RPE cells in culture which is supplemented with Activin A for an additional 10 days to 4 weeks to obtain RPE cells. The medium that is suitable for maintaining RPE cells in culture and that is further referred to as RPE Medium (RPEM) is preferably an essentially serum-free medium that is supplemented with serum replacement or a basal medium, like DMEM, that is supplemented with a lower percentage (preferably 1 to 2% by volume) of knockout serum/FBS or DMEM/F12 supplemented with B27.

Preferably said RPEM is supplemented with 10 to 1000 ng/ml, more preferably 20 to 500 ng/ml, even more preferably 50 to 200 ng/ml human Activin A. Preferably the RPEM is changed regularly.

When the first pigmentation sign appears, the Activin A may be withdrawn.

The RPE cells obtained according to the method of the invention are characterized by the expression of the marker genes Pax6, MiTF, ZO-1, Bestrophin and RPE-65. They are further negative for the expression of the neural retina progenitor cell marker Chx10.

In contrast to protocols known in the state of the art (see table 1), the method according to the invention advantageously yields a vast majority of RPE cells by 4 weeks with first pigmentation seen by 18 days.

The RPC and/or RPE cells obtained by the method according to the invention are particularly suited for use in screening, especially high-throughput screening, for candidate compounds that modify RPC and/or RPE cell fate, growth, differentiation and function. For this purpose the RPC and/or RPE cells are contacted with a library of candidate compounds, and their response, such as expression or down-regulation of one or more genes is determined by methods known in the art such as immunofluorescence, microarray analysis or flow cytometry in combination with suitable reporter constructs.

The RPC and/or RPE cells can thus be used for screening for candidate compounds that modulate RPC and/or RPE cell fate, growth, differentiation and function. This is carried out by contacting a cell with a candidate compound, and detecting the expression or activity of a certain gene or protein, wherein an alteration of expression or activity of that gene or protein as compared to a control indicates that said candidate compound is an compound that modulates RPC and/or RPE cell fate, growth, differentiation and function.

Detection of a response of a RPC and/or RPE cell can include detecting membrane dynamics such as secretion, endocystosis/phagocytosis or transcytosis, ion transport, detecting a nucleic and ribonucleic acid, preferably by nucleic acid hybridization, detecting a protein, its localization or detecting interaction between two or more proteins where an increase or decrease in said interaction, as compared to a control, indicates that said candidate compound modulates RPC and/or RPE cells cell fate, growth, differentiation and function.

Examples of nucleic acid hybridization assays useful in the screening method according to the invention include a Northern blot, a Southern blot, an array hybridization, an affinity chromatography, and an in situ hybridization, Detection of a protein in the screening method according to the invention can be accomplished by binding a protein with a detectable label. Examples of protein-based assays useful in the screening method according to the invention include capillary electrophoresis, a Western blot, mass spectroscopy, ELISA, immunochromatography, and immunocytochemistry.

Preferably, the control employed in the screening methods includes a cell contacted with the candidate compound at a lower concentration or a cell that is not contacted with the candidate compound.

Detection of a protein interaction is carried out by detecting specific binding of said candidate compound to one or more of said components. Examples of assays that can be employed in the screening method include a two-hybrid system and a gel-shift assay.

In addition the RPC and/or RPE cells obtained by the method according to the invention will be useful to make RPC and/or RPE cells from iPS cells derived from patients with genetic forms of various retinal diseases to model the disease in vitro and screen for substances that prevent or reverse cellular degeneration. The method according to the invention can also be used to generate mutant RPC and/or RPE cells by genetically modifying the initial pluripotent stem cells and subject them to the method according to the invention. The genetically modified RPC and/or RPE cells thus obtained are useful for investigating and elucidating the function of the respective modified gene.

Another object of the invention is the use of a proteinaceous gel comprising at least two, preferably at least three, components selected from the group consisting of Laminin, Collagen IV, Entactin, and Perlecan and comprising at least two, preferably three, most preferably four, growth factors selected from the group consisting of EGF, FGF2, NGF, PDGF, IGF-1 and TGF-beta, for differentiating pluripotent cells into polarized neural cysts.

Another object of the invention is the combined use of 3-D matrix and 2-D culture on filter membranes for differentiating pluripotent cells into RPE cells.

The cells obtained are particularly suitable for transplantation use in the generation of transplant tissue.

The RPE cells obtained by the method according to the invention can be used for subretinal transplantation to prevent and/or limit the progress of retinal degeneration and to preserve and/or improve of visual function.

The invention will now be illustrated by the following non-limiting examples, with reference to the figures, in which FIG. 1 shows the cell lineage of RPE cells.

Figure 2:
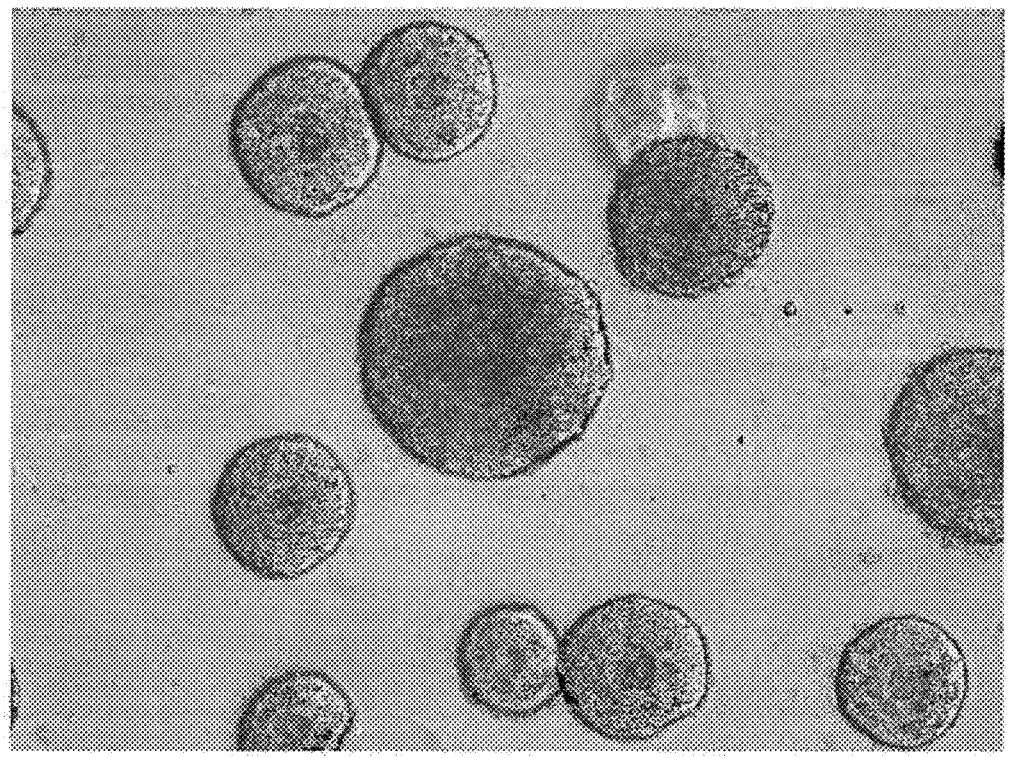

FIG. 2. shows the formation of cysts from human ES cell clumps cultured in the 3 dimensional differentiation model for 5 days. The lumen inside the cysts is clearly visible.

Figure 3:
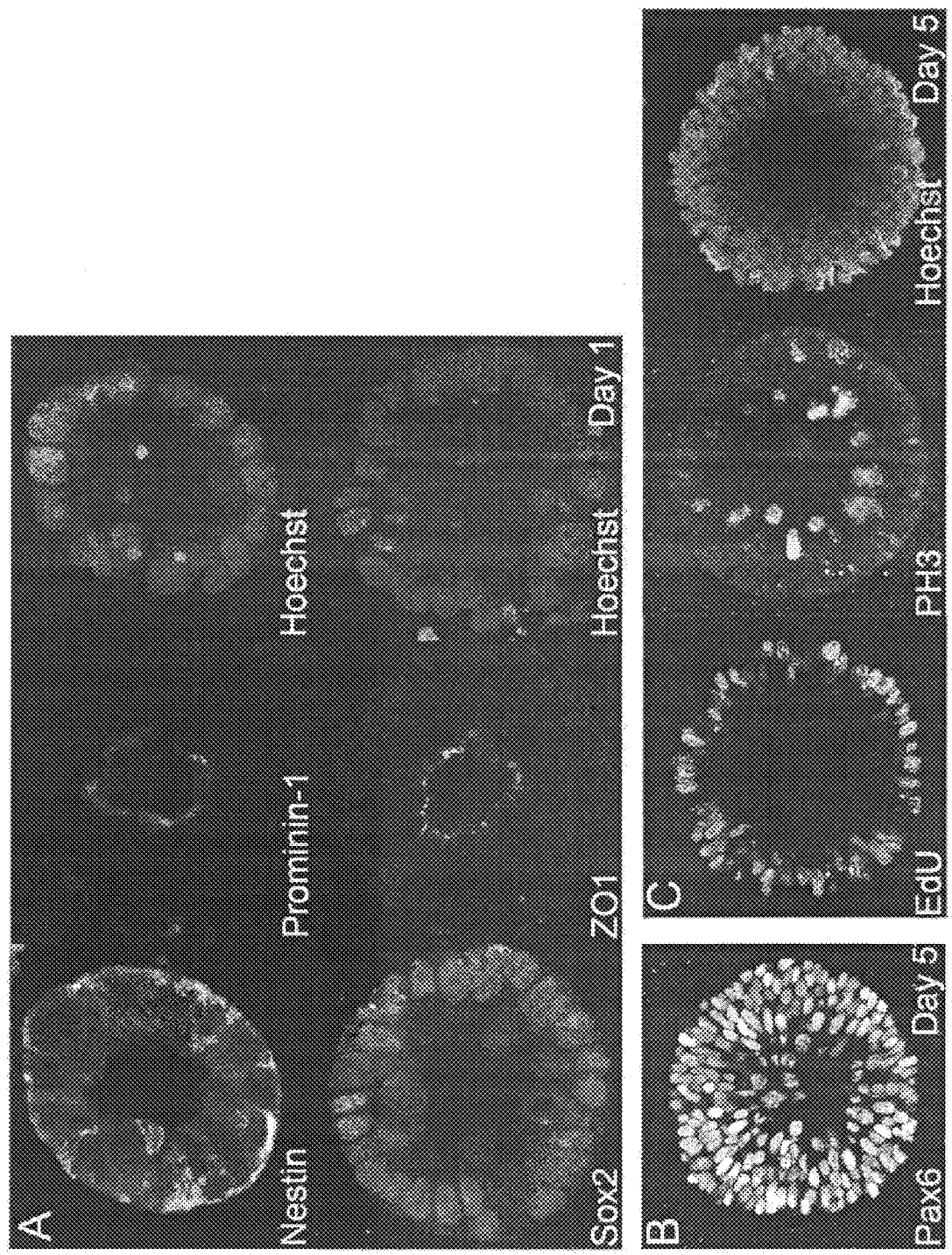

FIG. 3. demonstrates that the human ES cell-derived cysts are polarized neural progenitors. (A) Day-1 human ES cell-derived cysts expressed neural progenitor markers nestin and Sox2. Prominin-1 was only expressed in the apical side of the cysts indicating cell polarity. (B) The expression of neuroectodermal marker Pax6 is strongly expressed in Day-5 cysts. (C) Interkinetic nuclear migration confirmed the cell polarity inside the human ES cell-derived cysts. The M-phase cells were labeled by PH3. The S-phase cells were labeled by EdU. EdU is a thymidine analog that reacts with a fluorophore for visualization. M-phase occurred at apical side of the cysts and S-phase at basolateral side.

Figure 4:
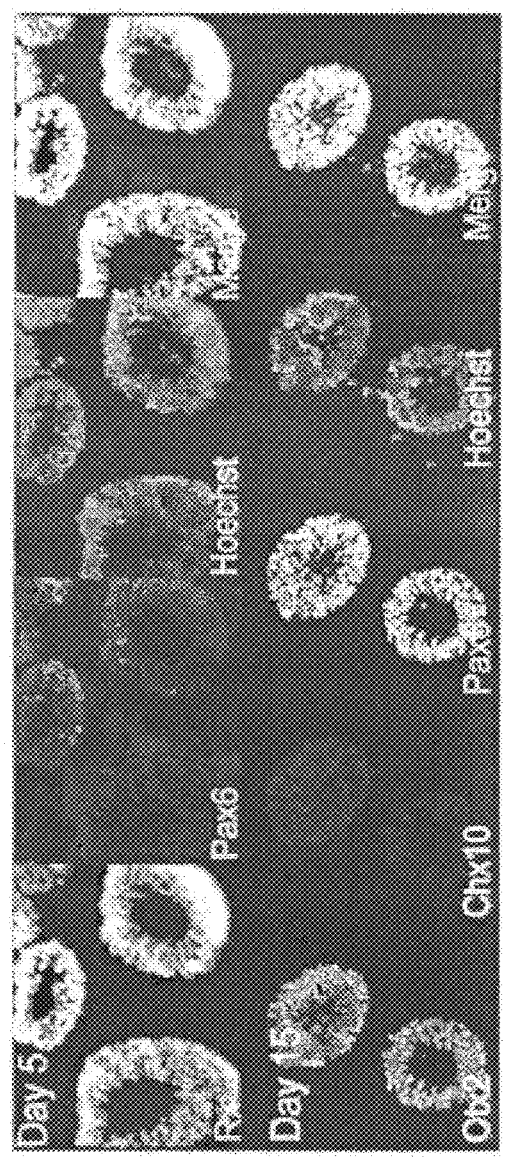

FIG. 4 shows that a large majority of the human ES cell-derived cysts were entering and maintaining eye field identity. (A) Immunostaining of retinal progenitor markers. (B) Percentage of cells positive for retinal markers by immunostaining. After 5 days of differentiation in the 3 dimensional model, more than 90% of the cells co-expressed eye field genes Otx2, Pax6 and Rx. On Day 15, around 60% of the cells expressed neural retina progenitor cell specific marker Chx10.

Figure 5:
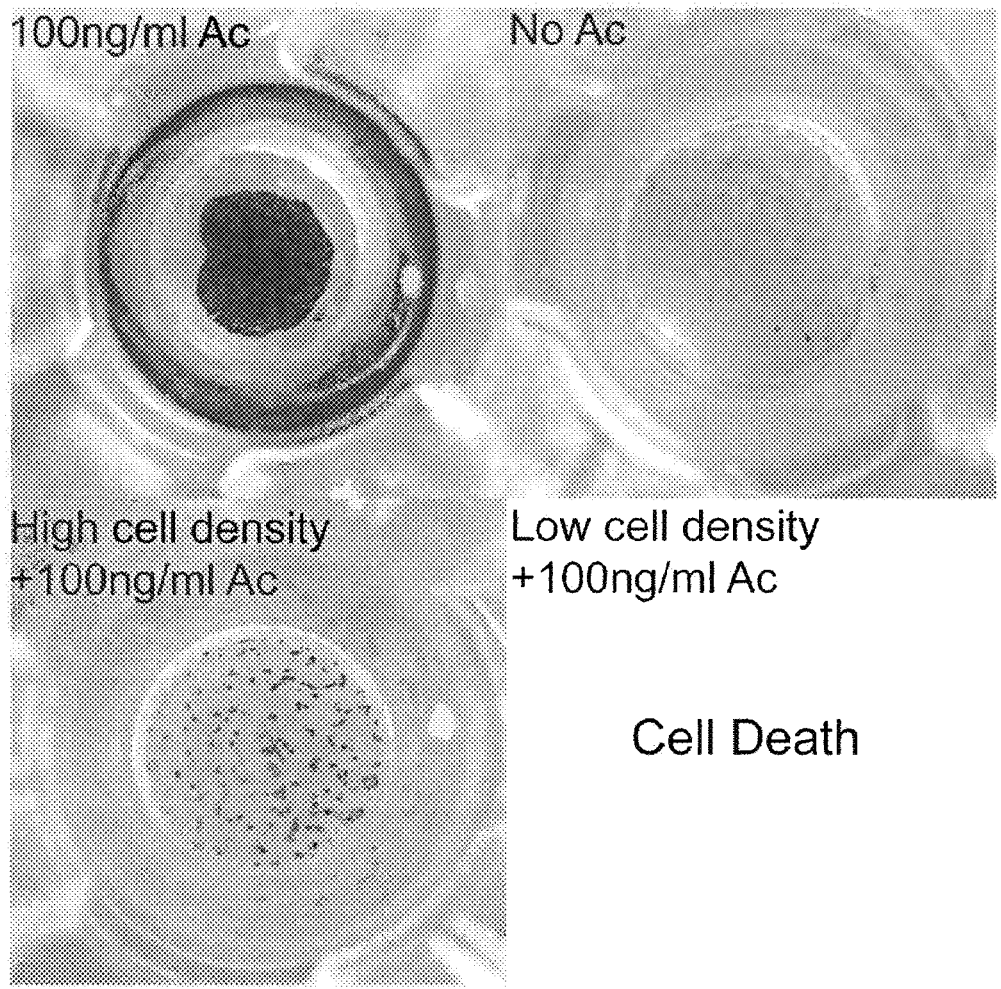

FIG. 5 illustrates that most of the cells turned pigmented on transwell filters with Activin A treatment at a certain cell density. Too high cell density caused regional pigmented clusters. Too low cell density caused cell death after Activin A treatment.

Figure 6:
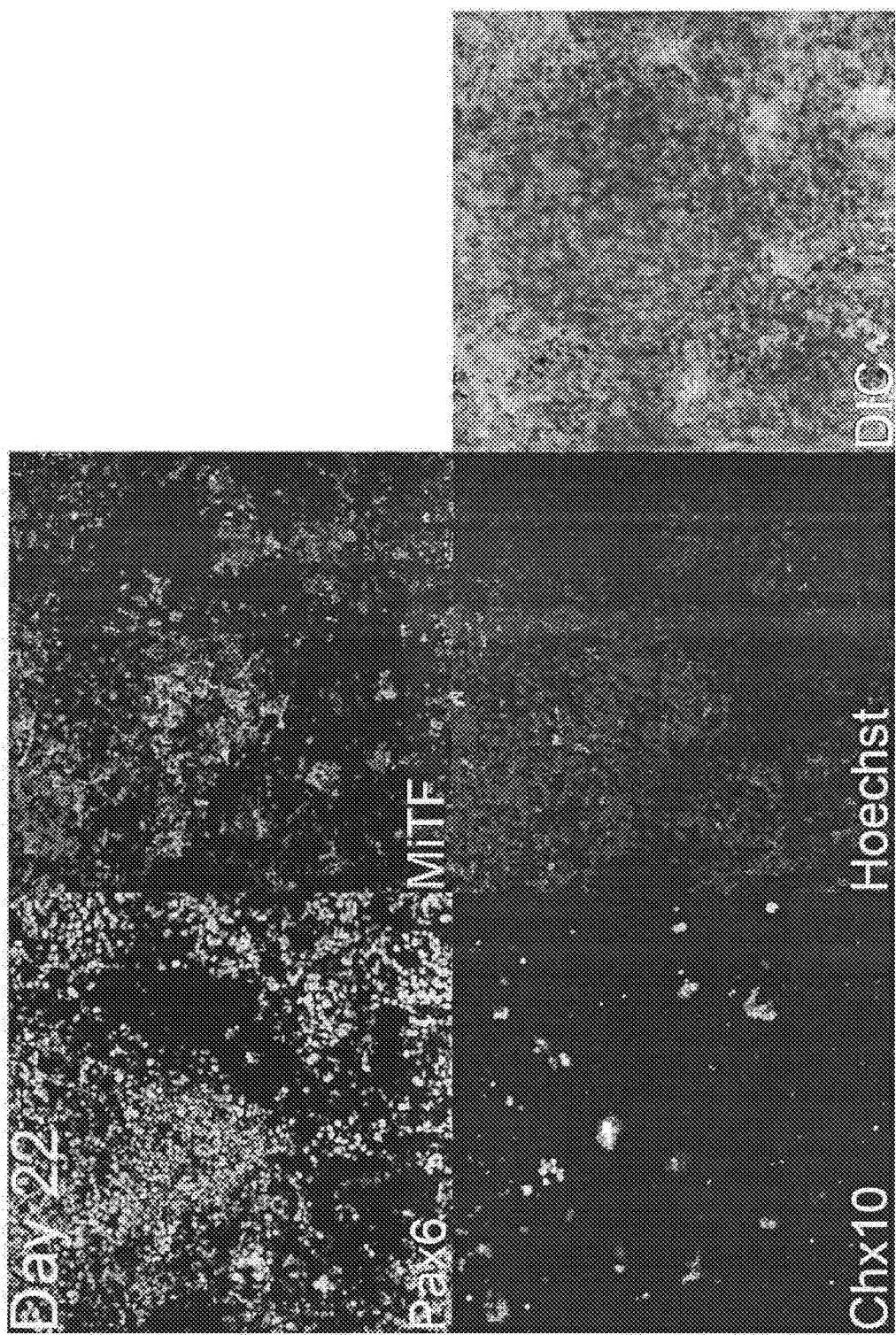

FIG. 6 shows Pax6, MiTF and Chx10 expression in immature RPE cells derived from human ES cells. Pigmentation was first seen around 18 days after initial differentiation of human ES cells. During differentiation, Pax6 was expressed stably. The expression of RPE-specific transcription factor MiTF increased progressively. The neural retina-specific transcription factor Chx10 was down-regulated in pigmented cells. The MiTF positive cells were exclusively Chx10 negative.

Figure 7:
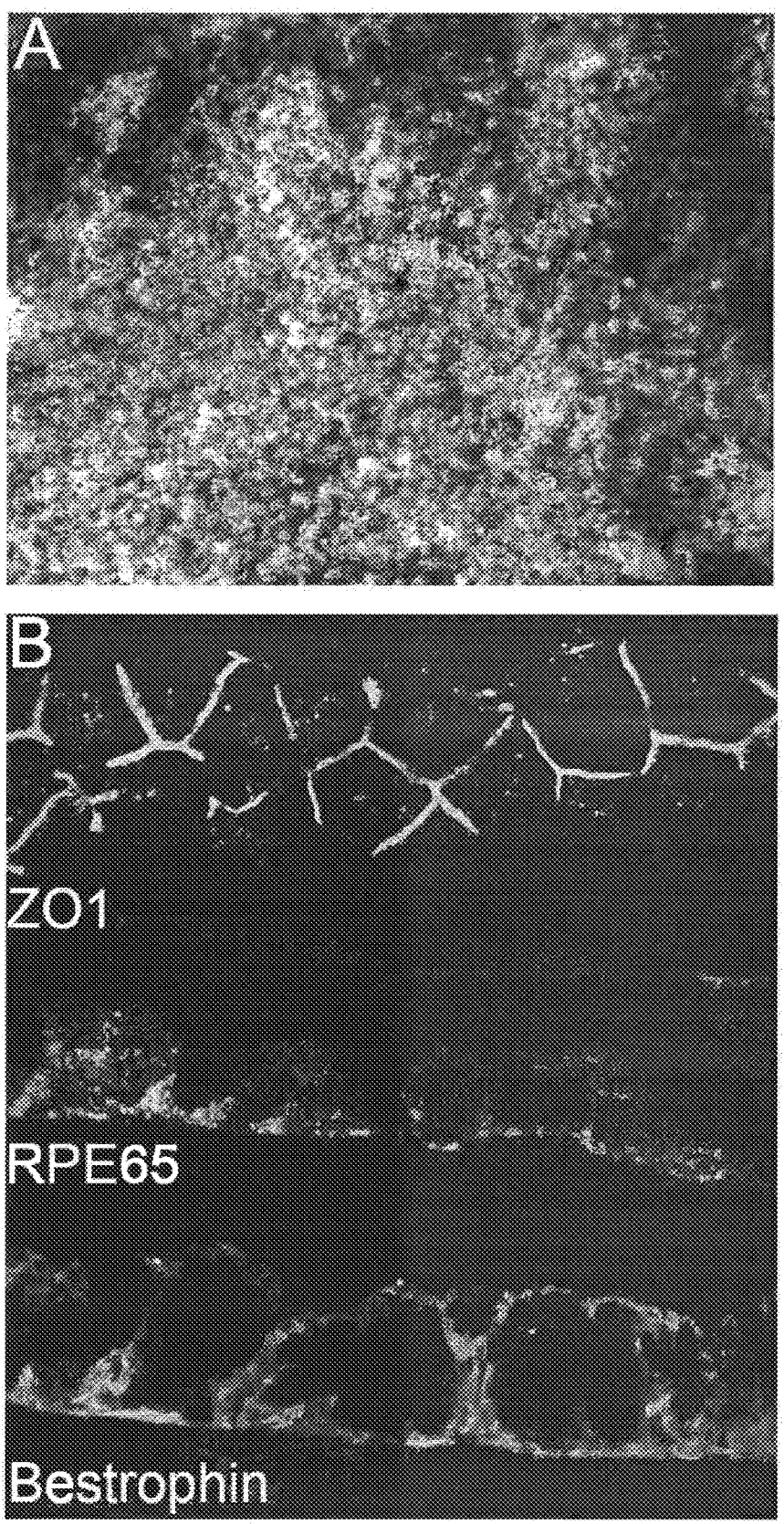

FIG. 7 contains a characterization of more mature human ES cell-derived RPE cells. A. The pigmented human ES cell-derived RPE cells have a polygonal shape. B. Immunostaining of ZO1, RPE65 and Bestrophin on 10 μm sections of human ES cell-derived RPE cells. RPE65 and Bestrophin were mostly located in the basal side of the cells.

Figure 8:
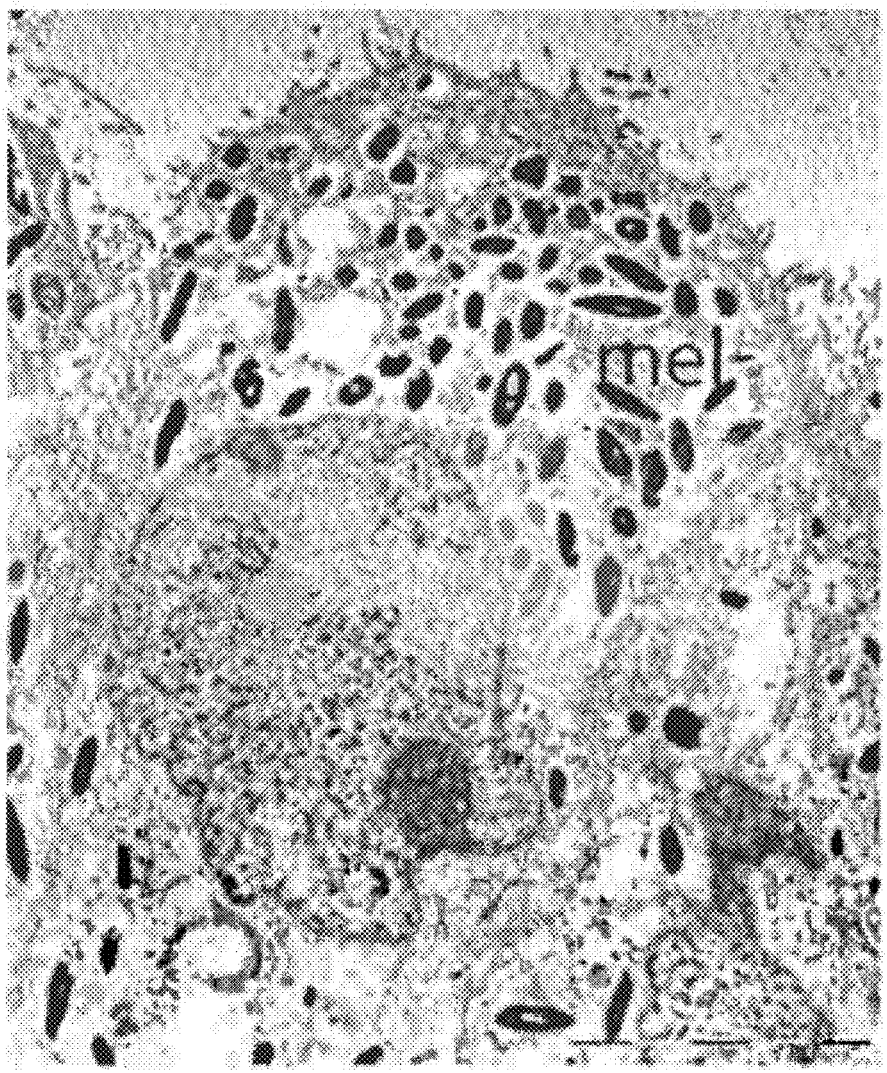

FIG. 8 shows an electron microscopic analysis of human ES cell-derived RPE cells. Microvilli were abundant at the apical side of the cells. The melanin granules at different maturation stages were in the apical half of the cells with the nuclei located at the basal half of the cells.

Figure 9:
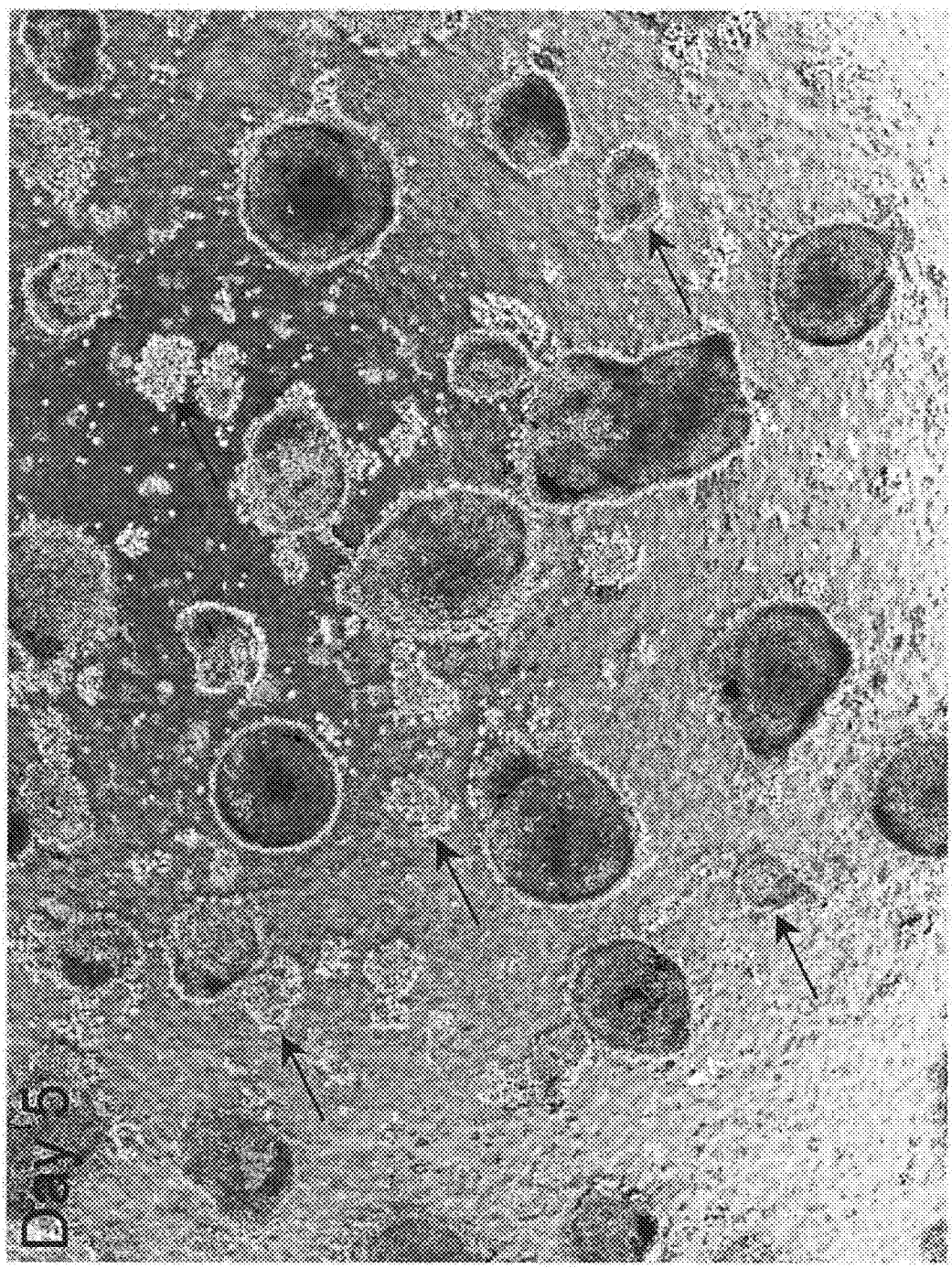

FIG. 9 and FIG. 10 demonstrate the low efficiency of cyst formation from hESCs in Collagen I. FIG. 9 shows a phase contrast image showing hESC clumps inefficiently formed cysts in Collagen I (1.8 mg/ml) after 5 days of differentiation. Many cell clumps were unable to form cysts (arrows). FIG. 10 shows fluorescent images of few formed cyst immunoreactive with both Pax6 and ZO-1 after 5 days of differentiation in Collagen I.

EXAMPLE

Experimental Protocol

Undifferentiated Human ES Cell Culture

The human embryonic stem (ES) cells H9 were maintained in mTeSR™1 medium (StemCell Technologies) at 37° C. in a humidified atmosphere of 5% CO2 and passaged with Dispase (StemCell Technologies). To improve cell survival during passaging, the Rho kinase inhibitor, Y-27632 (Calbiochem), was added in the culture media during the first 24 hrs after plating. For storage, the human ES colonies were suspended in mFreSR™ (StemCell Technologies), frozen in an isopropanol freezing container at −80° C. overnight and transferred into liquid nitrogen the next day.

Neural Differentiation of Human ES Cells in Three-Dimensional (3D) Model:

For neural differentiation, human ES cell colonies were partially dissociated into clumps with Dispase. The diameter of the cell clumps was in the range of 50-100 μm. The human ES cell clumps were washed once with N2B27 medium and pelleted by centrifugation (700 g, 3 min). Around $8 \times 10^5$ cells were resuspended in 30 μl N2B27 medium and embedded in 300 μl matrigel (BD). The ice-cold matrigel containing human ES cell clumps was plated as gel layer of about 1 mm thickness onto dishes. The matrigel was allowed to gel at 37° C. for 10 min followed by adding N2B27 medium into each dish. The cells were incubated in a humidified 37° C., 5% $CO_2$ incubator for five days to form polarized neural cysts (FIG. 2).

Further Differentiation into RPE Cells on Transwell Filters:

For retinal pigment epithelium (RPE) determination, the polarized neural cysts were taken out of the matrigel using cell recovery solution (BD) and washed in PBS once after 5 days of differentiation in the matrigel. To get rid of few non-cyst cells, we permitted large cysts to sink down to the bottom of the tube by gravity instead of centrifugation. TrypLE (Gibco) was then used to dissociate human ES cell-derived cysts into single cells by incubation in 37° C. water bath for 4 min with frequent flipping. Cells were pipetted gently into single cells, followed by spinning down (1000 g, 2 min), resuspending in N2B27 medium and going through 40 μm cell strainer (BD) to get single cell suspension. Dissociated cells were pelleted once more by centrifugation and plated onto growth factor reduced matrigel (BD) coated 6.5 mm Transwell® with 0.4 μm Pore Polyester Membrane Insert (Corning Costar) in N2B27 medium at a density of $2-4 \times 10^5$ cells/well.

On Day 6, attached cells were washed twice with RPE medium and then kept in RPE medium with 100 ng/ml human Activin A (Peprotech). The medium was changed every 3 days.

Media:
N2B27 medium
200 ml neurobasal medium (Gibco)
200 ml DMEM/F12 medium (Gibco)
4 ml B27 supplement (Gibco)
2 ml N-2 supplement
400 μl β-mercaptoethanol (final concentration 0.1 mM)
1 ml glutamate (final concentration 0.2 mM)
N2B27 should be stored at 4° C. and used within 1 week.

N2-supplement (100×)
625 μl Insulin stock solution
500 μl Apo-transferrin stock solution
335 μl BSA stock solution
16.5 μl Progesterone stock solution
50 μl Putrescine stock solution
5 μl Sodium selenite stock solution
3.468 ml DMEM/F12 medium (Gibco)
Batches of N2-supplement can be stored in aliquots at −20° C. for no longer than 3 weeks.
Insulin stock solution (25 mg/ml, Sigma): dissolve 100 mg/4 ml 0.01M sterile HCL. Insulin should be resuspended overnight at 4° C.
Apo-transferrin stock solution (100 mg/ml, Sigma): dissolve 500 mg/5 ml sterile H20.
BSA stock solution (75 mg/ml): dissolve in sterile PBS.
Progesterone stock solution (0.6 mg/ml, Sigma): dissolve 6 mg/10 ml ethanol and filter it.
Putrescine stock solution (160 mg/ml, Sigma): dissolve 1.6 g/10 ml H20 and filter it.
Sodium selenite stock solution (3 mM, Sigma): dissolve 2.59 mg/5 ml H20 and filter it.
The stocks are stored at −20° C.
RPE medium
200 ml DMEM+GlutaMax™-I (Gibco)
50 ml Knockout™ Serum Replacement (Gibco)
2.5 ml Non-Essential Amino Acid (Gibco)
1.25 ml Glutamate+β-mercaptoethanol(5 ml mM Glutamate+7 μl β-mercaptoethanol)

The invention claimed is:

1. A method of differentiating pluripotent stem cells into polarized retinal progenitor cells, comprising:
    (a) culturing pluripotent stem cell colonies in three-dimensional cell culture, in which the cells are embedded in a proteinaceous gel comprising at least two proteins selected from the group consisting of Laminin, Collagen IV, Entactin and Perlecan and comprising at least two growth factors selected from the group consisting of agonists of the EGF, FGF2, NGF, PDGF, IGF-1 and TGF-beta pathways in an essentially serum-free medium, until polarized neural cysts develop that contain a single lumen and consist of polarized cells, whereas after 5 days of differentiation in the three-dimensional culture, more than 90% of the cells co-expressed eye field genes Otx2, Pax6, and Rx; and
    (b) dissociating the polarized neural cysts into dispersed polarized retinal progenitor cells.

2. The method according to claim 1, wherein the pluripotent stem cell colonies are cultured in the three-dimensional culture for 4 to 7 days.

3. The method according to claim 1 wherein the pluripotent cells are selected from the group consisting of induced pluripotent stem cells, established embryonic stem cell lines, and combinations thereof.

4. The method according to claim 1, further comprising the subsequent differentiation of the polarized retinal progenitor cells obtained in (b) into retinal pigment epithelial (RPE) cells by culturing the dispersed polarized retinal progenitor cells in a cell culture medium supplemented with Activin A.

5. The method according to claim 1, further comprising the subsequent differentiation of the polarized retinal progenitor cells obtained in (b) into retinal pigment epithelium (RPE) cells by culturing the dispersed polarized retinal progenitor cells in two dimensional cell culture in a cell culture medium supplemented with Activin A.

6. The method according to claim 5, wherein the dispersed polarized retinal progenitor cells are cultured on a permeable microporous membrane placed in a dish or well containing said cell culture medium.

7. An in vitro cell culture produced by the method according to claim 1 comprising at least 80% polarized retinal progenitor cells and forming polarized neural cysts that contain a single lumen and consist of polarized cells, whereas more than 90% of the cells co-express eye field genes Otx2, Pax6, and Rx.

8. A method of screening a candidate compound for an effect on the viability, growth, metabolic function or differentiation of differentiating cells of the retinal lineage, comprising:
(a) contacting an in vitro cell population according to claim 7 with said candidate compound, and
(b) determining the effect of said candidate compound on the viability, growth, metabolic function or differentiation of said cells.

9. The method of claim 1, wherein the proteinaceous gel comprises at least three of said proteins.

10. The method of claim 1, wherein the proteinaceous gel comprises at least four of said proteins.

11. The method of claim 1, wherein the proteinaceous gel comprises at least four of said growth factors.

12. The method of claim 1, wherein the at least two growth factors are selected from EGF, FGF2, NGF, PDGF, IGF-1, and TGF-beta.

13. The method of claim 2, wherein the pluripotent stem cell colonies are cultured in the three-dimensional culture for 5 to 6 days.

14. A method of producing cells for use in transplantation comprising:
(a) culturing pluripotent stem cell colonies in three-dimensional cell culture, in which the cells are embedded in a proteinaceous gel comprising at least two proteins selected from the group consisting of Laminin, Collagen IV, Entactin and Perlecan and comprising at least two growth factors selected from the group consisting of agonists of the EGF, FGF2, NGF, PDGF, IGF-1 and TGF-beta pathways in an essentially serum-free medium, until polarized neural cysts develop that contain a single lumen and consist of polarized cells, whereas after 5 days of differentiation in the 3-dimensional culture, more than 90% of the cells co-expressed eye field genes Otx2, Pax6, and Rx;
(b) dissociating the polarized neural cysts into dispersed polarized retinal progenitor cells; and
(c) transplanting the retinal progenitor cells obtained in (b) subretinally.

15. A method of producing cells for use in transplantation comprising:
(a) culturing pluripotent stem cell colonies in three-dimensional cell culture, in which the cells are embedded in a proteinaceous gel comprising at least two proteins selected from the group consisting of Laminin, Collagen IV, Entactin and Perlecan and comprising at least two growth factors selected from the group consisting of agonists of the EGF, FGF2, NGF, PDGF, IGF-1 and TGF-beta pathways in an essentially serum-free medium, until polarized neural cysts develop that contain a single lumen and consist of polarized cells, whereas after 5 days of differentiation in the 3-dimensional culture, more than 90% of the cells co-expressed eye field genes Otx2, Pax6, and Rx;
(b) dissociating the polarized neural cysts into dispersed polarized retinal progenitor cells; and
(c) differentiating the polarized retinal progenitor cells into retinal pigment epithelial (RPE) cells by culturing the progenitor cells in the presence of Activin A.

16. A method of producing cells for use in transplantation comprising:
(a) culturing pluripotent stem cell colonies in three-dimensional cell culture, in which the cells are embedded in a proteinaceous gel comprising at least two proteins selected from the group consisting of Laminin, Collagen IV, Entactin and Perlecan and comprising at least two growth factors selected from the group consisting of agonists of the EGF, FGF2, NGF, PDGF, IGF-1 and TGF-beta pathways in an essentially serum-free medium until polarized neural cysts develop that contain a single lumen and consist of polarized cells, whereas after 5 days of differentiation in the 3-dimensional culture, more than 90% of the cells co-expressed eye field genes Otx2, Pax6, and Rx;
(b) dissociating the polarized neural cysts into dispersed polarized retinal progenitor cells; and
(c) differentiating the polarized retinal progenitor cells into retinal pigment epithelial (RPE) cells by culturing the progenitor cells in the presence of Activin A; and
(d) transplanting the retinal progenitor cells obtained in (c) subretinally.

* * * * *